(12) United States Patent
Wang et al.

(10) Patent No.: US 7,928,357 B2
(45) Date of Patent: *Apr. 19, 2011

(54) HIGH SPEED SCANNING PLATFORM FOR MICROARRAY SCANNER

(75) Inventors: Xianhua Wang, Beijing (CN); Hui Zhu, Beijing (CN); Guoliang Huang, Beijing (CN); Jing Cheng, Beijing (CN)

(73) Assignee: CapitalBio Corporation, Beijing (CN)

( * ) Notice: Subject to any disclaimer, the term of this patent is extended or adjusted under 35 U.S.C. 154(b) by 514 days.

This patent is subject to a terminal disclaimer.

(21) Appl. No.: 11/795,652

(22) PCT Filed: Jun. 2, 2005

(86) PCT No.: PCT/CN2005/000772
§ 371 (c)(1),
(2), (4) Date: Apr. 11, 2008

(87) PCT Pub. No.: WO2006/128322
PCT Pub. Date: Dec. 7, 2006

(65) Prior Publication Data
US 2009/0101805 A1    Apr. 23, 2009

(51) Int. Cl.
*H01J 3/14* (2006.01)
*H04N 1/04* (2006.01)
*G01N 33/50* (2006.01)
*F21V 9/16* (2006.01)
(52) U.S. Cl. .................................. 250/235; 250/458.1
(58) Field of Classification Search ............ 250/458.1, 250/461.2, 234, 235
See application file for complete search history.

(56) References Cited

U.S. PATENT DOCUMENTS

| 3,616,705 | A | * | 11/1971 | Platz ............................ 74/89.22 |
| 3,881,369 | A | * | 5/1975 | Looney ......................... 74/89.2 |
| 3,994,587 | A | * | 11/1976 | Yamamoto et al. ............. 356/73 |
| 4,281,557 | A | * | 8/1981 | Ohta et al. .................... 74/89.22 |
| 4,299,796 | A | * | 11/1981 | Hogen Esch .................... 422/63 |
| 4,332,472 | A | * | 6/1982 | Kato et al. .................... 204/642 |
| 4,495,149 | A | * | 1/1985 | Iwata et al. .................... 422/65 |
| 4,557,154 | A |   | 12/1985 | Iwata et al. |
| 4,772,453 | A | * | 9/1988 | Lisenbee ........................ 422/52 |
| 6,181,363 | B1 |   | 1/2001 | Satoh |
| 6,293,750 | B1 | * | 9/2001 | Cohen et al. ................ 414/744.4 |
| 6,332,636 | B1 | * | 12/2001 | Cohen et al. ................ 294/119.1 |
| 6,355,934 | B1 |   | 3/2002 | Osgood et al. |

(Continued)

FOREIGN PATENT DOCUMENTS

CN    2290063 Y    9/1998

(Continued)

OTHER PUBLICATIONS

U.S. Appl. No. 11/795,660, filed Jun. 2, 2005 by Wang at al. (Copy not attached.).

(Continued)

*Primary Examiner* — John R Lee
(74) *Attorney, Agent, or Firm* — Morrison & Foerster LLP

(57) ABSTRACT

The invention provides a scanning platform for high speed scanning of microarrays. The platform uses a novel flexible a metal strip/wheel linear driving system to convert rotary movement of motors into linear movement, thereby drives movement of a stage/microarray in the direction of scanning. The platform of the present invention provides high movement speed, high resolution, and low return deviation. It is also simple in structure and low in manufacturing cost.

18 Claims, 1 Drawing Sheet

U.S. PATENT DOCUMENTS

| | | |
|---|---|---|
| 6,374,982 B1* | 4/2002 | Cohen et al. ............. 198/346.2 |
| 6,471,916 B1 | 10/2002 | Noblett |
| 6,740,871 B1 | 5/2004 | Staton et al. |
| 7,615,758 B2* | 11/2009 | Wang et al. ............. 250/458.1 |
| 2002/0062202 A1 | 5/2002 | Arai |
| 2003/0030850 A1 | 2/2003 | Heffelfinger et al. |
| 2003/0161514 A1 | 8/2003 | Curry |
| 2003/0164814 A1 | 9/2003 | Starkweather et al. |
| 2003/0173509 A1* | 9/2003 | Ito et al. ............. 250/235 |
| 2004/0042007 A1 | 3/2004 | Osipchuk et al. |
| 2008/0252954 A1* | 10/2008 | Wang et al. ............. 359/202 |
| 2009/0046756 A1 | 2/2009 | Wang et al. |
| 2009/0101805 A1* | 4/2009 | Wang et al. ............. 250/234 |

FOREIGN PATENT DOCUMENTS

| | | |
|---|---|---|
| CN | 1387824 A | 1/2003 |
| CN | 1534288 A | 10/2004 |
| JP | 11014609 A | 1/1999 |
| JP | 2002-098639 A | 4/2002 |
| JP | 2003-015442 A | 1/2003 |
| WO | WO-2006/128321 A1 | 12/2006 |
| WO | WO-2006/128322 A1 | 12/2006 |
| WO | WO-2006/128325 A1 | 12/2006 |

OTHER PUBLICATIONS

U.S. Appl. No. 11/795,653, filed Jun. 3, 2005 by Wang et al. (Copy not attached.).

* cited by examiner

HIGH SPEED SCANNING PLATFORM FOR MICROARRAY SCANNER

TECHNICAL FIELD

This application is in the field of high speed scanning platform for microarray scanner.

BACKGROUND OF THE INVENTION

Developments in microarray-based detection devices have dramatically changed the biotechnology industry. The devices make it possible to analyze multiple biological samples simultaneously and detect rare transcripts in human. They also make it possible to obtain information from microarrays automatically within minutes instead of within months or even years without the help of the devices.

Microarrays typically comprise a plurality of polymers, such as oligonucleotides, peptides, and antibodies. The polymers are synthesized or deposited on a substrate in an array pattern, which can be labeled with optically detectable labels such as fluorescent tags or fluorophores. A typical microarray scanner uses laser as excitation light source, and use matching filters and photomultiplier tubes for detection. During scanning of a microarray, excitation light from the laser source hits different spots on the microarray. Fluorescent probes on the array emit Stokes-shifted light in response to the excitation light, and the emission light is collected by the photomultiplier tube. The resulting information on the microarray can be used for various purposes such as gene expression studies, mutational studies, genotyping, SNP studies, protein interaction analysis, as well as diagnosis and treatment of diseases.

Most of the microarray scanning systems use stepper motors and servo motors, which both require a linear driving mechanism to convert the rotary movement of the motors into linear movement. Traditional linear driving mechanisms include ball-screw driven mechanisms and belt driven mechanisms. Ball-screw driven mechanisms use a ball screw and a train of recirculating ball bearings contained in a nut to convert rotary movement into linear movement. Belt driven mechanisms utilize a belt that transforms the rotary movement of driving wheels into horizontal movement. When factors such as return deviation, lifetime, and load capacity are equivalent, the ball-screw driven mechanism provides medium moving speed and high precision of repetitivity, while belt driven mechanism provides high moving speed and low precision of repetitivity. Traditional microarray scanning devices thus either have a low scanning speed or a low precision of repetitivity. There is therefore a need for new scanning systems.

BRIEF SUMMARY OF THE INVENTION

The invention provides a scanning platform for moving a microarray in a plane comprising a stage for placing a microarray, wherein the stage is controlled by a first driving mechanism comprising a wheel and a flexible metal strip winding around the wheel, wherein two regions of the flexible metal strip are affixed to the stage so that rotation of the wheel moves the stage. In some embodiments, the wheel is coupled to a servo motor with low inertia. In some embodiments, one of the two regions is releasably affixed to the stage. The flexible metal strip may further comprise a prefastening region extending beyond the region that is releasably affixed to the stage.

In some embodiments, the scanning platform further comprises a second driving mechanism, wherein the first driving mechanism moves the stage in a scanning direction, and wherein the second driving mechanism moves the stage in a forwarding direction that is different from (such as perpendicular to) the scanning direction. In some embodiments, the second driving mechanism comprises a lead screw coupled to a stepper motor. In some embodiments, the first driving mechanism is positioned below the stage and above the second driving mechanism.

In another aspect, the invention provides a scanning platform for microarray scanning, comprising a base member including a first guiding rail; a slider that is slidably coupled to the first guiding rail, wherein the slider includes a second guiding rail that is perpendicular to the first guiding rail; a forwarding driving mechanism coupled to the slider which slidably moves the slider along the first guiding rail; a stage that is slidably coupled to the second guiding rail; and a scanning driving mechanism coupled to the stage which slidably moves the stage along the second guiding rail. In some embodiments, the scanning driving mechanism comprises a wheel and a flexible metal strip winding around the wheel, wherein two regions of the flexible metal strip are affixed to the stage so that rotation of the wheel moves the stage. In some embodiments, the scanning driving mechanism is coupled to a servo motor with low inertia. In some embodiments, the forwarding driving mechanism comprises a lead screw coupled to a stepper motor. In some embodiments, the scanning driving mechanism is mounted on the slider.

In one embodiment, the invention provides a scanning platform for microarray scanning comprising: a base member including a first guiding rail; a slider that is slidably coupled to the first guiding rail and wherein the slider includes a second guiding rail that is perpendicular to the second guiding rail; a lead screw coupled to the slider; a stepper motor coupled to the lead screw; a stage that is slidably coupled to the second guiding rail; a scanning driving mechanism comprising a wheel and a flexible metal strip winding around the wheel, wherein two regions of the flexible metal strip are affixed to the stage so that rotation of the wheel moves the stage; and a servo motor coupled to the scanning driving mechanism. In some embodiment, the scanning driving mechanism is mounted on the slider. In some embodiments, one of the two regions of the flexible metal strip is releasably affixed to the stage. In some embodiments, the flexible metal strip further comprises a prefastening region extending beyond the region that is releasably affixed to the stage.

DETAILED DESCRIPTION OF THE INVENTION

Figure 1:
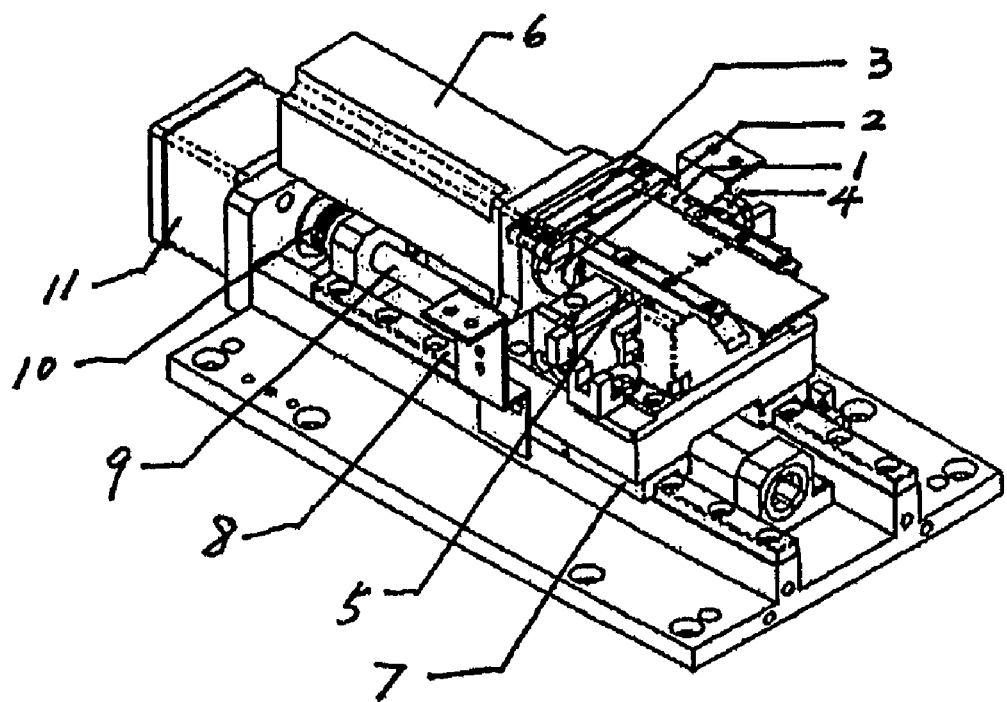
FIG. 1 is a schematic diagram of an exemplary scanning platform of the present invention.

The invention provides a scanning platform for moving a microarray in a plane comprising a stage for placing a microarray, wherein the stage is controlled by a driving mechanism comprising a wheel and a flexible metal strip winding around the wheel. Generally, the flexible metal strip winds around the wheel at least once. Two regions of the flexible metal strip, typically at opposite ends of a region of the flexible metal strip that winds around the wheel, are affixed to the stage. The wheel rotates around a rotation axis, and pulls the flexible metal strip. The flexible metal strip in turn pulls the stage, resulting in a linear movement of the stage. The rotary movement of the wheel is thus converted into linear movement through the flexible metal strip. Because the wheel can rotate either clockwise of counterclockwise, the stage can move in either direction.

The two regions of the flexible metal strip that are affixed to the stage can be affixed to the stage in any suitable manner. For example, the two regions can be affixed to two corners of the same end of the stage. The two regions can be affixed to the stage by any method known in the art. In some embodiments, one of the two regions of the flexible metal strip that are affixed to the stage is releasably affixed to the stage. The flexible metal strip may further comprise a prefastening region extending beyond the region that is releasably affixed to the stage. The end of the prefastening region may also be affixed to the stage. The prefastening region, in combination with the region of the flexible metal strip that is releasably affixed to the stage, can serve to adjust the tension of the region of the metal strip that winds around the wheel.

The flexible metal strip is generally made of a material with sufficient flexibility. Suitable materials for the flexible metal strip include, but are not limited to, steel, spring steel, and alloy steel. The flexible metal strip is generally very thin. Suitable thickness of the flexible metal strip include, but is not limited to, about 0.05 mm and 0.5 mm, such as between about 0.05 mm and about 1 mm.

In some embodiments, the wheel of the flexible metal strip/wheel driving mechanism is coupled to a servo motor with low inertia.

In another aspect, the present invention provides a scanning platform comprising a stage for placing the microarray to be scanned, wherein the stage (and the microarray placed thereon) can move in any desired manner in a two-dimensional plane. Specifically, the stage of the scanning platform is coupled to two driving mechanisms. One driving mechanism (the scanning driving mechanism) controls the repetitive movement of the stage in the direction(s) of scanning. Another driving mechanism (the forwarding driving mechanism) controls the forward movement of the stage in a direction that is different from (such as perpendicular to) the scanning direction. The two driving mechanisms work together to allow the whole microarray to be scanned.

In some embodiments, the first driving mechanism, i.e, the scanning driving mechanism, comprises a wheel and a flexible metal strip winding around the wheel, wherein two regions of the flexible metal strip are affixed to the stage so that rotation of the wheel moves the stage. The flexible metal strip/wheel driving mechanism described herein provides high speed and high precision of repetitivity, and is thus particularly useful for controlling the repetitive movement of the stage in the scanning direction in a high resolution microarray scanner.

On the other hand, the speed of the forward movement of the stage/microarray does not need to be very high, but its precision of repetitivity must be high. Accordingly, the forward driving mechanism can comprise a lead screw (such as a lead screw coupled to a stepper motor). In some embodiments, the lead screw is connected to a motor via a connecting rod.

In some embodiments, the stage is positioned on top of the scanning driving mechanism, which is in turn positioned on top of the forwarding driving mechanism. During scanning, the stage (along with the microarray placed thereon) moves relative to the scanning driving mechanism in the scanning direction. The scanning driving mechanism (along with the stage and the microarray chip placed thereon) moves in the direction of the forward movement.

The invention also provides a scanning platform comprising a base member including a first guiding rail; a slider that is slidably coupled to the first guiding rail, wherein the slider includes a second guiding rail that is perpendicular to the first guiding rail; a forwarding driving mechanism coupled to the slider which slidably moves the slider along the first guiding rail; a stage that is slidably coupled to the second guiding rail; and a scanning driving mechanism coupled to the stage which slidably moves the stage along the second guiding rail. In some embodiments, the scanning platform comprises a base member including a first guiding rail; a first slider that is slidably coupled to the first guiding rail, wherein the first slider includes a second guiding rail that is perpendicular to the first guiding rail; a forwarding driving mechanism coupled to the first slider which slidably moves the first slider along the first guiding rail; a second slider that is slidably coupled to the second guiding rail; a stage mounted on the second slider; and a scanning driving mechanism coupled to the stage which slidably moves the stage and the second slider along the second guiding rail.

In some embodiments, the scanning driving mechanism comprises a wheel and a flexible metal strip winding around the wheel, wherein two regions of the flexible metal strip are affixed to the stage so that rotation of the wheel moves the stage. In some embodiments, one of the two regions of the flexible metal strip is releasably affixed to the stage. In some embodiments, the flexible metal strip further comprises a prefastening region extending beyond the region that is releasably affixed to the stage.

In some embodiments, the scanning driving mechanism is actuated by, i.e., coupled to, a servo motor (such as a servo motor with low inertia). The scanning driving mechanism (including the motor) may be mounted on the slider and moves along the first guiding rail in the direction of forward movement.

The forwarding driving mechanism may comprise a lead screw coupled to a motor (such as a stepper motor). In some embodiments, the lead screw is connected to the motor via a connecting rod.

The first guiding rail on the base member may either be mounted on the base member or be an integral part of the base member. Similarly, the second guiding rail on the slider may either be mounted on the slider (or the first slider) or be an integral part of the base member. The guiding rails can be made of any materials that are grind-resistant, such as polished stainless steel. The guiding rails may further be coated with polytetrafluoroethylene (PTFE) (commonly available under the trade name TEFLON).

The base member and the slider may further include brackets. The first and second guiding rails extend longitudinally between these brackets. Specifically, the first guiding rail includes a first end and a second end. The first end is fixedly coupled to a first bracket on the base member and the second end fixedly coupled to a second bracket on the base member. The ends of the second guiding rail may be fixedly coupled to brackets on the slider in a similar manner.

In some embodiments, the scanning platform further comprises mechanical switches and photoswitches in the scanning direction and/or the forwarding direction. The mechanical switch may be positioned on the first or second guiding rail to limit (or alter the direction of) movement of the slider or stage. The photoswitch may be used for determining the position of the slider/stage. In some embodiments, the scanning platform comprises an optical grating for determining the position of the stage.

In one embodiment, the scanning platform comprises a base member including a first guiding rail; a slider that is slidably coupled to the first guiding rail and wherein the slider includes a second guiding rail that is perpendicular to the second guiding rail; a lead screw coupled to the slider; a stepper motor coupled to the lead screw; a stage that is slidably coupled to the second guiding rail; a scanning driving mechanism comprising a wheel and a flexible metal strip winding around the wheel, wherein two regions of the flexible metal strip are affixed to the stage so that rotation of the wheel moves the stage; and a servo motor coupled to the scanning driving mechanism. In another embodiment, the scanning platform comprises a base member including a first guiding rail; a first slider that is slidably coupled to the first guiding rail and wherein the first slider includes a second guiding rail that is perpendicular to the second guiding rail; a lead screw coupled to the first slider; a stepper motor coupled to the lead screw; a second slider that is slidably coupled to the second guiding rail; a stage mounted on the second slider, a scanning driving mechanism comprising a wheel and a flexible metal strip winding around the wheel, wherein two regions of the flexible metal strip are affixed to the stage so that rotation of the wheel moves the stage and the second slider; and a servo motor coupled to the scanning driving mechanism.

FIG. 1 shows one embodiment of an exemplary scanning platform. As shown in FIG. 1, stage 1 is mounted on second slider 5, which is slidably coupled to second guiding rail 4. Thin steel strip 3 is affixed to stage 1 and winds around wheel 2. Scanning motor 6 drives the thin steel strip/wheel system, which slidably moves second slider 5/stage along second guiding rail 4. Second guiding rail 4, wheel 2, thin steel strip 3 and scanning motor 6 thus together make the scanning driving mechanism that moves the stage. Second guiding rail 4 is positioned on first slider 7. Stage 1, controlled by the scanning driving mechanism, moves relative to first slider 7 in the direction of scanning.

First guiding rail 8, lead screw 9, connecting rod 10 and stepper motor 11 together make the forwarding driving mechanism. Under the control of the forwarding driving mechanism, first slider 7, on which the scanning driving mechanism is positioned, moves forward in a direction that is perpendicular to the scanning direction. During scanning, the stage moves in both the forwarding direction and the scanning direction, and thus allows the whole microarray be scanned at high speed and with high precision.

Figure 2:
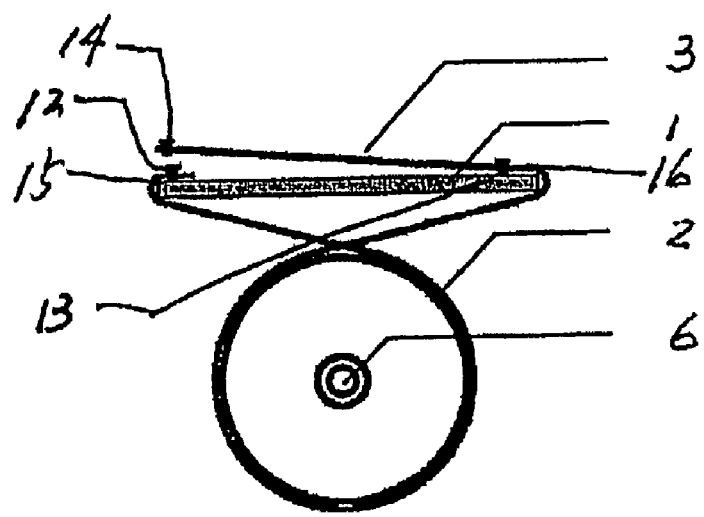
FIG. 2 is a schematic diagram of an exemplary thin steel strip/wheel linear driving system of the scanning platform of the present invention.

FIG. 2 shows one embodiment of the thin steel strip/wheel driving system of the present invention. The driving system comprises thin steel strip 3 and wheel 2. Wheel 2 is actuated by low inertia servo motor 6, and can rotate clockwise or counterclockwise. Thin steel strip 3 winds around wheel 2 once. Region 15 and region 16 of the flexible metal strip, which are at opposite ends of the metal strip region that winds around the wheel, are affixed to two corners of the same end of stage 1 by screws 12 and 13. Region 16 is releasably affixed to the stage. In this embodiment, the flexible metal strip extends beyond region 16, with its end further affixed on the stage by screw 14. The portion of the flexible metal strip between screw 13 and 14 serves a prefastening function, that is, the tension of the strip around the wheel can be changed by adjusting the prefastening region of the flexible metal strip. The driving mechanism converts the rotary movement of wheel 2 into repetitive linear movement through use of thin steel strip 3. The system as shown can achieve a scanning speed of 10-20 Hz (within a 10 mm range). Furthermore, it provides high precision of repetitivity, thereby solves the problem associated with traditional belt-driven mechanisms.

Although the invention is described mostly in the context of a micrcoarray scanner, those of skill in the art will understand that the invention is also useful in other applications. Furthermore, although the foregoing invention has been described in some detail by way of illustration and example for purpose of clarity and understanding, it will be apparent to those of skill in the art that certain changes and modifications can be practiced. Therefore, the description and examples should not be construed as limiting the scope of the invention, which is delineated by the appended claims. All the drawings are illustrated schematically. Angles and dimensions are not to scale.

What is claimed is:

1. A scanning platform for moving a microarray in a plane comprising a stage for placing a microarray, wherein the stage is controlled by a first driving mechanism comprising a wheel; and a flexible metal strip winding around the wheel, wherein two regions of the flexible metal strip are affixed to the stage so that rotation of the wheel moves the stage.

2. The scanning platform of claim 1, wherein one of the two regions is releasably affixed to the stage.

3. The scanning platform of claim 2, wherein the flexible metal strip further comprises a prefastening region extending beyond the region that is releasably affixed to the stage.

4. The scanning platform of claim 1, wherein the wheel is coupled to a servo motor with low inertia.

5. The scanning platform any of claim 1, further comprising a second driving mechanism, wherein the first driving mechanism moves the stage in a scanning direction, and wherein the second driving mechanism moves the stage in a forwarding direction that is different from the scanning direction.

6. The scanning platform of claim 5, wherein the second driving mechanism moves the stage in a forwarding direction that is perpendicular to the scanning direction.

7. The platform of claim 5, wherein the first driving mechanism is positioned below the stage and above the second driving mechanism.

8. The platform of claim 5, wherein the second driving mechanism comprises a lead screw coupled to a stepper motor.

9. A scanning platform for microarray scanning, comprising a base member including a first guiding rail; a slider that is slidably coupled to the first guiding rail, wherein the slider includes a second guiding rail that is perpendicular to the first guiding rail; a forwarding driving mechanism coupled to the slider which slidably moves the slider along the first guiding rail; a stage that is slidably coupled to the second guiding rail; and a scanning driving mechanism coupled to the stage which slidably moves the stage along the second guiding rail, and wherein the scanning driving mechanism comprises a wheel and a flexible metal strip winding around the wheel, wherein two regions of the flexible metal strip are affixed to the stage so that rotation of the wheel moves the stage.

10. The scanning platform of claim 9, wherein one of the two regions of the flexible metal strip is releasable affixed to the stage.

11. The scanning platform of claim 10, wherein the flexible metal strip further comprises a prefastening region extending beyond the region that is releasably affixed to the stage.

12. The scanning platform of claim 9, wherein the scanning driving mechanism is coupled to a servo motor with low inertia.

13. The scanning platform of claim 9, wherein the scanning driving mechanism is mounted on the slider.

14. The scanning platform of claim 9, wherein the forwarding driving mechanism comprises a lead screw coupled to a stepper motor.

15. A scanning platform for microarray scanning, comprising: a base member including a first guiding rail; a slider that is slidably coupled to the first guiding rail and wherein the slider includes a second guiding rail that is perpendicular to the second guiding rail; a lead screw coupled to the slider; a stepper motor coupled to the lead screw; a stage that is slidably coupled to the second guiding rail; a scanning driving mechanism comprising a wheel and a flexible metal strip winding around the wheel, wherein two regions of the flexible metal strip are affixed to the stage so that rotation of the wheel moves the stage; and a servo motor coupled to the scanning driving mechanism.

16. The scanning platform of claim 15, wherein the scanning driving mechanism is mounted on the slider.

17. The scanning platform of claim 15, wherein one of the two regions of the flexible metal strip is releasably affixed to the stage.

18. The scanning platform of claim 17, wherein the flexible metal strip further comprises a prefastening region extending beyond the region that is releasably affixed to the stage.

* * * * *